United States Patent
Zaias et al.

(10) Patent No.: US 9,216,159 B2
(45) Date of Patent: *Dec. 22, 2015

(54) INCREASED EFFECTIVENESS OF ALLYLAMINE DRUG COMPOUNDS FOR TOPICAL TREATMENT OF FUNGAL INFECTIONS OF THE SKIN AND SKIN APPENDAGES

(71) Applicant: BIOPHILE CORPORATION, LTD., Lumpinee, Patumwan Bangkok (TH)

(72) Inventors: Nardo Zaias, Miami Beach, FL (US); Pichit Suvanprakorn, Bangkok (TH); Panida Vayumhasuwan, Bangkok (TH)

(73) Assignee: BIOPHILE CORPORATION, LTD. (TH)

( * ) Notice: Subject to any disclaimer, the term of this patent is extended or adjusted under 35 U.S.C. 154(b) by 0 days.

This patent is subject to a terminal disclaimer.

(21) Appl. No.: 14/504,766

(22) Filed: Oct. 2, 2014

(65) Prior Publication Data

US 2015/0017234 A1  Jan. 15, 2015

Related U.S. Application Data

(63) Continuation of application No. 13/252,796, filed on Oct. 4, 2011, now Pat. No. 8,853,280, which is a continuation of application No. 12/012,647, filed on Feb. 5, 2008, now Pat. No. 8,052,984.

(60) Provisional application No. 60/899,433, filed on Feb. 5, 2007.

(51) Int. Cl.

| | |
|---|---|
| *A61K 31/137* | (2006.01) |
| *A61K 31/131* | (2006.01) |
| *A61K 9/127* | (2006.01) |
| *A61K 9/50* | (2006.01) |
| *A61K 47/10* | (2006.01) |
| *A61K 47/24* | (2006.01) |
| *A61K 47/26* | (2006.01) |

(52) U.S. Cl.
CPC ............... *A61K 31/137* (2013.01); *A61K 9/127* (2013.01); *A61K 9/50* (2013.01); *A61K 31/131* (2013.01); *A61K 47/10* (2013.01); *A61K 47/24* (2013.01); *A61K 47/26* (2013.01); *Y10S 514/944* (2013.01); *Y10S 514/946* (2013.01); *Y10S 514/947* (2013.01); *Y10S 514/975* (2013.01); *Y10S 977/773* (2013.01); *Y10S 977/906* (2013.01); *Y10S 977/907* (2013.01)

(58) Field of Classification Search
CPC ............ Y10A 977/773; Y10S 977/906; Y10S 514/944; Y10S 514/975; Y10S 514/946; Y10S 514/947; A61K 9/127; A61K 9/50; A61K 47/10; A61K 47/24; A61K 47/26; A61K 31/137; A61K 31/131
See application file for complete search history.

(56) References Cited

PUBLICATIONS

Tosti, et al, Onychomycosis Caused by Nondermatophytic Molds: Clinical Features and Response to Treatment of 59 Cases, 42 J Am. Acad. Dermatol. 217 (2000).*
First Examination Report; Government of India Patent Office; Mailed on Oct. 29, 2014 for Indian Patent Application No. 4438/DELNP/2009.
Extended European Search Report; Mailed on Oct. 23, 2013 for European Patent Application No. 12169658.7.

* cited by examiner

*Primary Examiner* — Sean Basquill
(74) *Attorney, Agent, or Firm* — Grimes & Yvon LLP

(57) ABSTRACT

The invention is an increased effectiveness of allylamine drug compounds for topical treatment of fungal infections of skin and skin appendages. The allylamine active ingredient is prepared in an acidic environment; the acidic environment altering the physiochemical properties of the active ingredient resulting in the active ingredient having a positive charge. The positive charge and enhancers used in the formula allow for increased penetration of the active ingredient through skin and skin appendages. The positively charged active ingredients are either dissolved in the vehicle directly or dissolved in a plurality of beads suspended in the vehicle. The bead structure minimizes the molecular diffusion of the positively charged active ingredient and a catalytic species through the bead structure, thus stabilizes the positively charged active ingredient inside the bead by impeding the interaction of the positively charged active ingredient and the catalytic species, and thereby extending the shelf life of the positively charged active ingredient.

13 Claims, No Drawings

INCREASED EFFECTIVENESS OF ALLYLAMINE DRUG COMPOUNDS FOR TOPICAL TREATMENT OF FUNGAL INFECTIONS OF THE SKIN AND SKIN APPENDAGES

CROSS REFERENCE

This application is a continuation of U.S. Ser. No. 13/252,796, filed Oct. 4, 2011, which is a continuation of U.S. Ser. No. 12/012,647, filed Feb. 5, 2008, which claims the benefit of U.S. Provisional Patent Application No. 60/899,433 filed on Feb. 5, 2007. The entire teachings of the above-referenced applications are incorporated herein by reference.

FIELD OF INVENTION

The invention is an increased effectiveness of allylamine drug compounds for topical treatment of fungal infections of the skin and skin appendages. One embodiment of the invention is the use of terbinafine as the active ingredient for treating various diseases, such as onychomycosis. For the first time the penetration of the nail bed corneocytes, either through or around the nail plate, is achieved by topical application of the present invention.

The increased effectiveness for topical treatment of fungal infections of the skin and skin appendages uses an allylamine as the active ingredient. One novel feature of the invention is that the positively charged allylamine drug compounds and penetrating enhancers used in the invention make it effective for topical treatment of fungal infections of the skin and skin appendages. The active ingredient is prepared in an acidic environment; the acidic environment altering the physiochemical properties of the active ingredient resulting in the active ingredient having a positive charge. It is this positive charge and the enhancers used in the formula that allow for increased effectiveness for topical treatment of fungal infections of the skin and skin appendages. The positively charged active ingredients are either dissolved in a delivery vehicle directly or dissolved in a plurality of beads suspended in the vehicle. The preferred delivery vehicle is transparent, but alternative delivery vehicles with various degrees of transparency may be used. The bead structure minimizes the molecular diffusion of the positively charged active ingredient and a catalytic species through the bead structure, thus stabilizes the positively charged active ingredient inside the bead by impeding the interaction of the positively charged active ingredient and the catalytic species, and thereby extending the shelf life of the positively charged active ingredient.

BACKGROUND

A major goal of the pharmaceutical and cosmeceutical industry is the development of effective products. Topical products are of interest since they are not invasive, they can be applied directly to the target area, and thus have fewer side effects. The development of effective topical products needs a multidisciplinary approach since the active ingredients must have optimum solubility, adequate stability and optimum concentration at the target area. The skin and skin appendages have different structures and compositions, so what is needed is an invention that can overcome their hard to penetrate barriers.

Therefore, it is an objective of the present invention to make products that are effective for topical treatment of fungal infections of the skin and skin appendages.

SUMMARY

The invention is an increased effectiveness of allylamine drug compounds for topical treatment of fungal infections of the skin and skin appendages. Various allylamines can be used as the active ingredient. A novel feature of the invention is that the positively charged allylamine drug compounds and penetrating enhancers used in the invention make it effective for topical treatment of fungal infections of the skin and skin appendages. The active ingredient is prepared in an acidic environment; the acidic environment altering the physiochemical properties of the active ingredient resulting in the active ingredient having a positive charge. It is this positive charge and the enhancers used in the formula that allow for increased effectiveness of allylamine drug compounds for topical treatment of fungal infections of the skin and skin appendages. The positively charged active ingredients are dissolved in a delivery vehicle directly or may be dissolved in a plurality of beads suspended in the vehicle. The bead structure minimizes the molecular diffusion of the positively charged active ingredient and a catalytic species through the bead structure, thus stabilizes the positively charged active ingredient inside the bead by impeding the interaction of the positively charged active ingredient and the catalytic species, and thereby extending the shelf life of the positively charged active ingredient.

In one preferred embodiment, the active ingredient is an allylamine selected from the group consisting of terbinafine hydrochloride or naftifine hydrochloride. The active ingredient is dissolved in at least one solubilizer and the pH of the resulting mixture is adjusted to less than 7.5 using a buffer. The active ingredient is deemed to be completely dissolved in the allylamine/buffer/solubilizer mixture. The active ingredient can be added to the buffer first then the solubilizer(s) is added to completely dissolve the active ingredient or vice versa. In this embodiment, terbinafine hydrochloride is added to the buffer such that the final concentration of terbinafine hydrochloride in the bead structure is 0.001 to 6% (weight/weight). The preferred acidic buffer is a citrate buffer with a pH of less than 7.5. The preferred pH range of the acidic buffer is 3.5 to 6. The preferred citrate buffer is prepared by mixing citric acid and sodium citrate, however other commonly known acidic buffers may be used. An ultrasonic probe or other similar means may be used to assist the dissolution process.

In order to completely dissolve the allylamine of the preferred embodiment, at least one solubilizer is used to dissolve the allylamine. In the preferred embodiment, the addition of ethanol was used as the solubilizer, however other known solubilizers may be used. The active ingredient is deemed to be completely dissolved in the allylamine/buffer/solubilizer mixture.

At least one enhancer is then added to the mixture. The enhancers used in the preferred embodiment were ethanol, polysorbate 80, phospholipids, propylene glycol and/or 1,3-butanediol. However, other known enhancers such as other alcohols, fatty alcohols, fatty acids, fatty acid esters, polyols, amides, pyrrolidone derivatives, surfactants, phospholipids and terpenes may be used in alternative embodiments.

Antioxidants are then added to the above mixture and stirred until dissolved. The antioxidants in the preferred embodiment were used to protect the active ingredients. The use of antioxidants for stabilizing preparations is common knowledge in the pharmaceutical industry. The antioxidants of the present invention are not specifically chosen for their antioxidant effect on skin. In the preferred embodiment, alpha-tocopherol, butylated hydroxytoluene and butylated hydroxylanisole are used as the antioxidants. However, other known antioxidants may be used in alternative embodiments.

Preservatives are then added to the mixture. In the preferred embodiment, methyl 4-hydroxybenzoate and propyl 4-hydroxybenzoate are dissolved in 1,3-butanediol. The preservative mixture is then added to the allylamine mixture above. In alternative embodiments, other types of preservatives may be used.

A humectant is then added to the mixture. The humectants used in the preferred embodiments are 1,3-butanediol or propylene glycol. However, other known humectants such as glycerin, sorbitol and polyethylene glycol may be used in alternative embodiments.

A viscosity increasing agent(s) is then added to the mixture. In the preferred embodiment carbopol 940 and/or hydroxyethyl cellulose dispersed in 1,3-butanediol or propylene glycol is used as the viscosity increasing agent(s). However, other known gelling agents or viscosity increasing agents such as other acrylic polymers, cellulose derivatives, natural gums and poloxamers may be used in alternative embodiments.

If needed, other acids or bases commonly used in pharmaceutical preparations such as hydrochloric acid, sodium hydroxide and potassium hydroxide may be used to adjust the final pH to less than 7.5, preferably 3.5 to 6.0.

A delivery vehicle is added and the resulting mixture placed in a storage container for future use or transferred into a dispenser for application to skin, skin appendages, and nails.

In a preferred alternate embodiment, a vehicle containing a plurality of beads is used. In this embodiment, the invention is prepared as previously discussed but sodium alginate is used to increase the mixture viscosity instead of carbopol 940 and/or hydroxyethyl cellulose. Also, instead of placing the mixture in a storage container or a dispenser, the resulting mixture is then passed through a dispensing tip into a hardening agent. The effect of the interaction between the aliquoted solution and the hardening agent is to harden the outer most exposed area of each aliquot to form a bead. In the preferred embodiment, the mixture is passed through a dispensing tip having an orifice diameter of 0.2-5 millimeters. A plurality of beads is produced by the aliquoted mixture. Although a dispensing tip was used for the preferred embodiment, other commonly known dispensing methods may be used.

Although 0.1-20% calcium chloride solution was used as the hardening agent in the preferred embodiment other types of hardening agents may be used. The type of hardening agent selected will depend on the polymer used to form the beads. For example, in alginate beads, a divalent cation is usually used, such as calcium ion or barium ion, especially calcium chloride and barium chloride.

Each bead preferably measures 2-2.5 millimeters in size. However, the beads may range from 0.2 to 10 millimeters in size. The bead may be negatively charged due to the negative nature of alginate, although some of the alginate would cross-link with the calcium ions.

The plurality of beads are then sieved and washed with an aqueous buffer solution. In the preferred embodiment, citrate buffer was used to wash the plurality of beads; however, other types of buffer solutions may be used. It is preferable that the citrate buffer has a pH of less than 7.5, and preferably has a pH of 3.5 to 6.0. In the alternate preferred embodiment, the plurality of beads is then delivered to a fluidized bed dryer by a motor-driven sieve belt. The plurality of beads is dried by vertically blowing them through the fluidized bed dryer or another type of mechanical delivery and drying method.

The plurality of beads is then transferred to an agitator containing a gel base and mixed by a propeller until homogenous. Other gelling agents may be used to form the gel base, such as cellulose derivatives and xanthan gum. The resulting bead/gel mixture is then placed in a storage container for future use or placed into a dispensing container for application.

In the preferred embodiment, the gel is prepared by dispersing a gelling agent in a humectant. A buffer with a pH of less than 7.5, preferably 3.5 to 6.0, is added to the dispersion and stirred until homogeneous. Preservatives are dissolved in the humectant and added to the mixture and stirred until homogenous.

In the preferred alternate embodiment, the gelling agent(s) used was carbopol 940 and/or hydroxylethyl cellulose. However, other known gelling agents or viscosity increasing agents such as other acrylic polymers, cellulose derivatives, natural gums and poloxamers may be used in alternative embodiments. The pH of the final gel is preferably 3.5 to 6.0 and may be adjusted using other commonly known pH adjusting solutions such as hydrochloric acid, sodium hydroxide and potassium hydroxide.

In the preferred and alternate preferred embodiments, the gel acts as a delivery vehicle or base for the beads. The gel also acts as a storage medium. The base is not critical in the delivery of the active ingredient to the target location. In some embodiments the delivery vehicle may be transparent while in other embodiments the delivery vehicle may be opaque or colored. Transparency, opaqueness and color are characteristic of the type of vehicle used in the formulation. For example, if waxes are used as the vehicle, the vehicle would be white in color.

Due to the fact that so many beads in the alternate preferred embodiment are contained in the base, the beads are in contact with one another and it is very hard to observe any changes in the base. In fact, the only way to determine if active ingredient is diffusing through the bead wall is to analyze the gel using high performance liquid chromatography (HPLC).

DETAILED DESCRIPTION

The invention is an increased effectiveness of allylamine drug compounds for topical treatment of fungal infections of the skin and skin appendages. Various allylamines can be used as the active ingredient. A novel feature of the invention is that the positively charged allylamine drug compounds and penetrating enhancers used in the invention make it effective for topical treatment of fungal infections of the skin and skin appendages. The active ingredient is prepared in an acidic environment; the acidic environment altering the physiochemical properties of the active ingredient resulting in the active ingredient having a positive charge. It is this positive charge and the enhancers used in the formula that allow for increased effectiveness of the active ingredient for topical treatment of fungal infections of the skin and skin appendages. The positively charged active ingredients are dissolved in a delivery vehicle directly or may be dissolved in a plurality of beads suspended in the vehicle. The bead structure minimizes the molecular diffusion of the positively charged active ingredient and a catalytic species through the bead structure, thus stabilizes the positively charged active ingredient inside the bead by impeding the interaction of the positively charged active ingredient and the catalytic species, and thereby extending the shelf life of the positively charged active ingredient.

In the preferred embodiment, the active ingredient is dissolved in at least one solubilizer and the pH of the resulting mixture is adjusted to less than 7.5 using a buffer. The active ingredient is deemed to be completely dissolved in the allylamine/buffer/solubilizer mixture. The active ingredient can be added to the buffer first then the solubilizer(s) is added to completely dissolve the active ingredient or vice versa. An ultrasonic probe or other similar means may be used to assist the dissolution process. Antioxidants, enhancers, preservatives, humectants and viscosity increasing agents are then added to the mixture.

In an alternate embodiment, a vehicle containing a plurality of beads is used. In this embodiment, the bead structure is prepared by dissolving the active ingredient in at least one solubilizer and the pH of mixture is adjusted to less than 7.5 using a buffer. An ultrasonic probe or other similar means may be used to assist the dissolution process. Antioxidants, enhancers, preservatives and humectants are then added to the mixture. A viscosity increasing agent dissolved in a solvent is added to the mixture. The resulting mixture is then passed through dispensing tips into a hardening agent. As each aliquot of the dispensed mixture encounters the hardening agent a bead is formed. The dispensing step produces a plurality of beads. The plurality of beads are then sieved and washed with an aqueous buffer solution. The plurality of beads is then delivered to a fluidized bed dryer using a motor driven sieve belt. The plurality of beads is then dried by vertically blowing them through the fluidized bed dryer. The plurality of beads then are transferred to an agitator containing a gel base and mixed by a propeller until homogenous. The resulting bead/gel mixture is then placed in a storage container for future use or placed into a dispensing container for application.

In the preferred embodiment, the active ingredient is an allylamine selected from the group consisting of terbinafine hydrochloride or naftifine hydrochloride. However, in other embodiments, the active ingredient may be selected from any class of compound that is commercially available. Terbinafine is a white to off-white fine crystalline powder and has very limited solubility in water (<0.001%). Terbinafine hydrochloride is a white to off-white fine crystalline powder with a melting point of approximately 205 degrees Celsius. The pKa value is 7.10 and the pH of a solution (0.5%) in methanol/water (4:6) is approximately 4.7 at 25 degrees Celsius. The solubility of terbinafine hydrochloride is 0.63% (w/v) in water. Terbinafine in topical preparation in the marketplace (1%) is usually in basic solution (pH>7.5).

In one of the preferred embodiments, the terbinafine hydrochloride is the allylamine used to make the invention. In this embodiment, terbinafine hydrochloride is added to an acidic buffer such that the final concentration of terbinafine hydrochloride in the bead structure is 0.001 to 6% (weight/weight). The preferred acidic buffer is a citrate buffer with a pH of less than 7.5. The preferred pH range of the acidic buffer is 3.5 to 6. The preferred citrate buffer is prepared by mixing citric acid and sodium citrate. Although citrate buffer was used in the preferred embodiment, other commonly known acidic buffer solutions may be used, such as phosphate buffer or acetate buffer.

In order to completely dissolve the allylamine of the preferred embodiment, at least one solubilizer is used to dissolve the allylamine. In the preferred embodiment, the addition of ethanol was used as the solubilizer. An ultrasonic probe was used to assist the dissolution of the terbinafine hydrochloride. The active ingredient is deemed to be completely dissolved in the allylamine/buffer/solubilizer mixture. Although ethanol was used in the preferred embodiment, other known solubilizers such as other alcohols, glycols, surfactants and complexing agents may be used in alternative embodiments. Furthermore, other commercially available mechanism may be used to assist the dissolution of the allylamine.

At least one enhancer is then added to the mixture. The enhancers used in the preferred embodiment were ethanol, polysorbate 80, phospholipids, propylene glycol and/or 1,3-butanediol. However, other known enhancers such as other alcohols, fatty alcohols, fatty acids, fatty acid esters, polyols, amides, pyrrolidone derivatives, surfactants, phospholipids and terpenes may be used in alternative embodiments.

Antioxidants are then added to the above mixture and stirred until dissolved. The antioxidants in the preferred embodiment were used to protect the active ingredients. The use of antioxidants for stabilizing preparations is common knowledge in the pharmaceutical industry. The antioxidants of the present invention are not specifically chosen for their antioxidant effect on skin.

In the preferred embodiment, alpha-tocopherol, butylated hydroxytoluene and butylated hydroxylanisole are used as the antioxidants. However, other known antioxidants may be used in alternative embodiments.

Preservatives are then added to the mixture. In the preferred embodiment, methyl 4-hydroxybenzoate and propyl 4-hydroxybenzoate are dissolved in 1,3-butanediol. The preservative mixture is then added to the allylamine mixture above. In alternative embodiments, other types of preservatives may be used.

A humectant is then added to the mixture. The humectants used in the preferred embodiments are 1,3-butanediol or propylene glycol. However, other known humectants such as glycerin, sorbitol and polyethylene glycol may be used in alternative embodiments. The humectant promotes the retention of moisture in the invention.

A viscosity increasing agent(s) is then added to the mixture. In the preferred embodiment carbopol 940 and/or hydroxyethyl cellulose dispersed in 1,3-butanediol or propylene glycol was used as the viscosity increasing agent(s). However, other known gelling agents or viscosity increasing agents such as acrylic polymers, cellulose derivatives, natural gums and poloxamers may be used in alternative embodiments.

If needed, other acids or bases commonly used in pharmaceutical preparations such as hydrochloric acid, sodium hydroxide and potassium hydroxide may be used to adjust the final pH to less than 7.5, preferably 3.5 to 6.0.

The procedure for making one embodiment of the invention would be as follows:

1. Dissolve terbinafine HCl in 5-50% ethanol in a closed system to completely dissolve terbinafine HCl.
2. Add 18.6-92.3% citrate buffer with a pH of less than 7.5 (preferably 3.5-6.0) in step 1 using an ultrasonic probe.
3. Add 0.001-0.2% alpha-tocopherol, butylated hydroxytoluene, and butylated hydroxyl anisole to the mixture and stir until dissolved.
4. Dissolve 0.1-0.2% methyl 4-hydroxybenzoate and 0.01-0.1% propyl 4-hydroxybenzoate in 0.5-2% 1,3-butanediol and add to the mixture.
5. Disperse 0.1-2.5% of carbomer 940 in 2.00-20% of 1,3-butanediol.
6. Add citrate buffer with a pH of less than 7.5 (preferably 3.5-6.0) to the carbomer dispersion in step 5 and stir until homogeneous.
7. Add the mixture in step 4 to the carbomer dispersion in step 6 and stir until homogeneous.
8. Adjust pH of the mixture to less than 7.5 (preferably 3.5-6.0) using hydrochloric acid or potassium hydroxide solution if needed, and stir until homogeneous.

In the preferred embodiment described above, the following ingredients were used:

| | | |
|---|---|---|
| Terbinafine Hydrochloride | 0.001 to 6% | active ingredient |
| (±) α-Tocopherol | 0.001 to 0.2% | antioxidant |
| Carbopol 940 | 0.1 to 2.5% | viscosity increasing agent |
| Butylated Hydroxytoluene | 0.001 to 0.2% | antioxidant |
| Butylated Hydroxyanisole | 0.001 to 0.2% | antioxidant |
| Methyl 4-Hydroxybenzoate | 0.1 to 0.2% | preservative |
| Propyl 4-Hydroxybenzoate | 0.01 to 0.1% | preservative |
| 1,3-Butanediol | 2 to 20% | humectant, enhancer |
| Ethanol | 5 to 50% | Solubilizer, enhancer |
| Citric Acid Monohydrate | | buffer |
| Sodium Citrate | | buffer |

The citrate buffer is used to make pH of less than 7.5 (preferably 3.5-6.0).

In another preferred embodiment, the following ingredients were used:

| | | |
|---|---|---|
| Terbinafine Hydrochloride | 0.001 to 6% | active ingredient |
| (±) α-Tocopherol | 0.001 to 0.2% | antioxidant |
| Carbopol 940 | 0.1 to 2.5% | viscosity increasing agent |
| Butylated Hydroxytoluene | 0.001 to 0.2% | antioxidant |
| Butylated Hydroxyanisole | 0.001 to 0.2% | antioxidant |
| Methyl 4-Hydroxybenzoate | 0.1 to 0.2% | preservative |
| Propyl 4-Hydroxybenzoate | 0.01 to 0.1% | preservative |
| 1,3-Butanediol | 2 to 20% | humectant, enhancer |
| Polysorbate 20 | 1 to 40% | Solubilizer, enhancer |
| Citric Acid Monohydrate | | buffer |
| Sodium Citrate | | buffer |

The citrate buffer is used to make pH of less than 7.5 (preferably 3.5-6.0).

In third preferred embodiment, the following ingredients were used:

| | | |
|---|---|---|
| Terbinafine Hydrochloride | 0.001 to 6% | active ingredient |
| (±) α-Tocopherol | 0.001 to 0.2% | antioxidant |
| Carbopol 940 | 0.1 to 2.5% | viscosity increasing agent |
| Butylated Hydroxytoluene | 0.001 to 0.2% | antioxidant |
| Butylated Hydroxyanisole | 0.001 to 0.2% | antioxidant |
| Methyl 4-Hydroxybenzoate | 0.1 to 0.2% | preservative |
| Propyl 4-Hydroxybenzoate | 0.01 to 0.1% | preservative |
| Propylene Glycol | 2 to 20% | humectant, enhancer |
| Polysorbate 80 | 1 to 40% | Solubilizer, enhancer |
| Citric Acid Monohydrate | | buffer |
| Sodium Citrate | | buffer |

The citrate buffer is used to make pH of less than 7.5 (preferably 3.5-6.0).

In a fourth preferred embodiment, the following ingredients were used:

| | | |
|---|---|---|
| Terbinafine Hydrochloride | 0.001 to 6% | active ingredient |
| (±) α-Tocopherol | 0.001 to 0.2% | antioxidant |
| Carbopol 940 | 0.1 to 2.5% | viscosity increasing agent |
| Hydroxyethyl cellulose | 0.1 to 6% | viscosity increasing agent |
| Butylated Hydroxytoluene | 0.001 to 0.2% | antioxidant |
| Butylated Hydroxyanisole | 0.001 to 0.2% | antioxidant |
| Methyl 4-Hydroxybenzoate | 0.1 to 0.2% | preservative |
| Propyl 4-Hydroxybenzoate | 0.01 to 0.1% | preservative |
| 1,3-Butanediol | 2 to 20% | humectant, enhancer |
| Ethanol | 5 to 50% | solubilizer, enhancer |
| Phospholipids | 1 to 20% | solubilizer, enhancer |
| Citric Acid Monohydrate | | buffer |
| Sodium Citrate | | buffer |

The citrate buffer is used to make pH of less than 7.5 (preferably 3.5-6.0).

In a fifth preferred embodiment, the following ingredients were used:

| | | |
|---|---|---|
| Terbinafine Hydrochloride | 0.001 to 6% | active ingredient |
| (±) α-Tocopherol | 0.001 to 0.2% | antioxidant |
| Carbopol 940 | 0.1 to 2.5% | viscosity increasing agent |
| Butylated Hydroxytoluene | 0.001 to 0.2% | antioxidant |
| Butylated Hydroxyanisole | 0.001 to 0.2% | antioxidant |
| Methyl 4-Hydroxybenzoate | 0.1 to 0.2% | preservative |
| Propyl 4-Hydroxybenzoate | 0.01 to 0.1% | preservative |
| Propylene Glycol | 2 to 20% | humectant, enhancer |
| Cholesterol | 1 to 25% | stabilizer |
| Polysorbate 80 | 1 to 40% | Solubilizer, enhancer |
| Citric Acid Monohydrate | | buffer |
| Sodium Citrate | | buffer |

The citrate buffer is used to make pH of less than 7.5 (preferably 3.5-6.0).

In an alternate embodiment of the preferred invention, a vehicle containing a plurality of beads is used to make the invention. In this preferred embodiment, the bead structure is prepared by dissolving the active ingredient in a solubilizer and the pH of resulting mixture is adjusted to less than 7.5 using a buffer. An ultrasonic probe or other similar means may be used to assist the dissolution process. Antioxidants, enhancers, preservatives and humectants are then added to the mixture using the same procedure as the preferred embodiments previously described. A viscosity increasing agent is then added to the mixture. The viscosity increasing agent used in the this embodiment was sodium alginate dispersed in 1,3-butanediol. However, other known viscosity increasing agents may be used in alternative embodiments.

The resulting mixture is then passed through a dispensing tip into a hardening agent. The effect of the interaction between the aliquoted solution and the hardening agent is to harden the outer most exposed area of each aliquot to form a bead. In the preferred embodiment, the mixture is passed through a dispensing tip having an orifice diameter of 0.2-5 millimeters. A plurality of beads is produced by the aliquoted mixture. Although a dispensing tip was used for the preferred embodiment, other commonly known dispensing methods may be used.

In the preferred alternate embodiment, a 0.1-20% calcium chloride solution was used as the hardening agent. Other types of hardening agents may be used. The type of hardening agent selected will depend on the polymer used to form the beads. For example, in alginate beads, a divalent cation is usually used, such as calcium ion or barium ion, especially calcium chloride and barium chloride.

In the alternate preferred embodiment, each bead measures 2-2.5 millimeters in size. However, the beads may range from 0.2 to 10 millimeters in size. The bead may be negatively charged due to the negative nature of alginate, although some of the alginate would cross-link with the calcium ions. The applicants have not yet performed any experiments to determine cross-linking density and drug release rates through the bead shell.

The plurality of beads are then sieved and washed with an aqueous buffer solution. In the preferred embodiment, citrate buffer was used to wash the plurality of beads. It is preferable that the citrate buffer has a pH of less than 7.5, and preferably has a pH of 3.5 to 6.0. In alternative embodiments, other types of buffer solutions may be used. In the alternate preferred embodiment, the plurality of beads is then delivered to a fluidized bed dryer by a motor-driven sieve belt. The plurality of beads is dried by vertically blowing them through the fluidized bed dryer. Although a motor-driven sieve belt and a fluidized bed dryer were used in the preferred embodiment, other types of mechanical delivery and drying methods may be used.

The plurality of beads is then transferred to an agitator containing a gel base and mixed by a propeller until homogenous. Other gelling agents may be used to form the gel base, such as cellulose derivatives and xanthan gum. The resulting bead/gel mixture is then placed in a storage container for future use or placed into a dispensing container for application.

In the preferred embodiment, the gel is prepared by dispersing a gelling agent in a humectant. A buffer with a pH of less than 7.5, preferably 3.5 to 6.0, is added to the dispersion and stirred until homogeneous. Preservatives are dissolved in the humectant and added to the mixture and stirred until homogenous.

In the preferred alternate embodiment, the gelling agent(s) used was carbopol 940 and/or hydroxylethyl cellulose. However, other known gelling agents or viscosity increasing agents such as acrylic polymers, cellulose derivatives, natural gums and poloxamers may be used in alternative embodiments. The pH of the final gel is preferably 3.5 to 6.0 and may be adjusted using other commonly known pH adjusting solutions such as hydrochloric acid, sodium hydroxide and potassium hydroxide.

In the preferred and alternate embodiments, the gel acts as a delivery vehicle or base for the beads. The gel also acts as a storage medium. The base is not critical in the delivery of the active ingredient to the target location. In some embodiments the delivery vehicle may be transparent while in other embodiments the delivery vehicle may be opaque or colored. Transparency, opaqueness and color are characteristic of the type of vehicle used in the formulation. For example, if waxes are used as the vehicle, the vehicle would be white in color.

Due to the fact that so many beads in the alternate preferred embodiment are contained in the base, the beads are in contact with one another and it is very hard to observe any changes in the base. In fact, the only way to determine if active ingredient is diffusing through the bead wall is to analyze the gel using high performance liquid chromatography (HPLC).

The procedure for making one alternate embodiment of the invention's beads would be as follows:
1. Dissolve terbinafine HCl in 5-50% ethanol in a closed system to completely dissolve terbinafine HCl.
2. Add 18.6-92.3% citrate buffer with a pH of less than 7.5 (preferably 3.5-6.0) in step 1 using an ultrasonic probe.
3. Add 0.001-0.2% alpha-tocopherol, butylated hydroxytoluene, and butylated hydroxyanisole to the mixture and stir until dissolved.
4. Dissolve 0.1-0.2% methyl 4-hydroxybenzoate and 0.01-0.1% propyl 4-hydroxybenzoate in 0.5-2% 1,3-butanediol and add to the mixture.
5. Disperse 0.5 to 2.0% sodium alginate in 2-10% 1,3-butanediol and add to the mixture.
6. Pass the mixture through tips with a diameter of 0.2-5 mm to 0.1-20% calcium chloride solution and beads are formed.
7. Sieve the beads and wash them using citrate buffer with a pH of less than 7.5 (preferably 3.5-6.0).
8. Deliver the beads using a sieve belt driven by a motor to a fluidized bed dryer and dry them by vertically blowing them through the fluidized bed dryer.
9. Transfer the beads to an agitator containing carbopol gel and mix them using a propeller until homogeneous.

A step by step procedure of making one embodiment of the invention's gel base is as follows:
1. Disperse 0.1-2.5% of carbomer 940 in 2.00-20% of 1,3-butanediol.
2. Add citrate buffer with a pH of less than 7.5 (preferably 3.5-6.0) to the carbomer dispersion and stir until homogeneous.
3. Dissolve 0.1-0.2% methyl 4-hydroxybenzoate and 0.01-0.1% propyl 4-hydroxybenzoate in 0.5-2% 1,3-butanediol and add to the mixture.
4. Adjust pH of the mixture to less than 7.5 (preferably 3.5-6.0) using hydrochloric acid or potassium hydroxide solution if needed, and stir until homogeneous.

The following data, obtained during development of the invention, shows terbinafine hydrchloride amount (mg) in each bead normalized to a weight of 0.0073 grams per bead (average weight of 10 beads). The average amount of terbinafine HCl per bead is 0.095±0.004 mg.

|  | Bead No. | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| Bead Weight (g) | 0.0085 | 0.0075 | 0.0070 | 0.0071 | 0.0082 | 0.0065 | 0.0067 | 0.0067 | 0.0075 | 0.0073 |
| Terbinafine HCl (mg) per bead | 0.091 | 0.096 | 0.093 | 0.095 | 0.093 | 0.098 | 0.090 | 0.104 | 0.097 | 0.095 |

Each bead is a protective envelop which is designed to extend the shelf life of the positively charged active ingredient contained within each individual bead. In the preferred alternate embodiment, the bead structure is more like a solid than an aqueous gel base. Therefore it is difficult for the molecules inside the beads to diffuse and react. Thus the bead structure helps stabilize the ingredients inside.

As long as the bead is in the delivery vehicle, the bead retains and limits the active ingredient to enter the delivery vehicle. This allows the use of a bead and the delivery vehicle to form combinations desirable for other ingredients which may be interactive in regular vehicles.

Analysis of one preferred embodiment shows the bead structure helps stabilize the ingredients inside. When using terbinafine hydrochloride as the active ingredient, it has been shown that the predicted shelf-life of terbinafine hydrochloride as used in the present invention is greater when compared to terbinafine hydrochloride in gel alone (without the bead structure of the present invention).

|  | Terbinafine HCl concentration (g %) | |
| --- | --- | --- |
| time (days) | Gel (stored at ambient temperature) | Beads in Gel (stored at 30° C.) |
| 0 | 1.0922 | 1.0411 |

| time (days) | Gel (stored at ambient temperature) | Beads in Gel (stored at 30° C.) |
|---|---|---|
|    |        | 1.0029 |
|    |        | 0.9437 |
|    |        | 0.9752 |
|    |        | 0.9967 |
| 11 | 1.0131 |        |
|    | 1.0144 |        |
| 39 |        | 1.0542 |
|    |        | 1.0540 |
|    |        | 1.0199 |
| 41 |        | 1.0655 |
|    |        | 0.9250 |
|    |        | 0.9566 |
| 68 |        | 0.9790 |
|    |        | 0.9731 |
|    |        | 1.0214 |
| 70 |        | 1.0449 |
|    |        | 0.9741 |
|    |        | 1.0200 |
| 253 | 0.975 |        |
|    | 0.9583 |        |

By extrapolating the zero order kinetics of the data above (Terbinafine concentration (g %)=−0.000195 time (days)+ 1.0158), the predicted shelf-life of terbinafine in gel is 532 days, while the zero order kinetics of terbinafine beads in gel (Terbinafine concentration (g %)=−0.000091 time (days)+ 1.0111) gives the predicted shelf-life of 1134 days.

In prototype development, the composition of each bead was so protective, that the allylamine terbinafine hydrochloride was retained in bead. Analysis of prototype samples was conducted during development found the amount of terbinafine HCl leaking from the beads to be 0.27%, 4.25%, and 6.37% of terbinafine HCl in gel base after 1, 46, and 84 days, respectively.

In the preferred alternate embodiment, the following ingredients were used to make the present invention:

| Terbinafine hydrochloride | 0.001 to 6% | active ingredient |
|---|---|---|
| (±) α-Tocopherol | 0.001 to 0.2% | antioxidant |
| Sodium Alginate | 0.5 to 2.0% | viscosity increasing agent |
| Carbopol 940 | 0.1 to 2.5% | viscosity increasing agent |
| Butylated Hydroxytoluene | 0.001 to 0.2% | antioxidant |
| Butylated Hydroxyanisole | 0.001 to 0.2% | antioxidant |
| Methyl 4-Hydroxybenzoate | 0.1 to 0.2% | preservative |
| Propyl 4-Hydroxybenzoate | 0.01 to 0.1% | preservative |
| 1,3-Butanediol | 2 to 20% | humectant, enhancer |
| Ethanol | 5 to 50% | solubilizer, enhancer |
| Citric Acid Monohydrate |  | buffer |
| Sodium Citrate |  | buffer |

The citrate buffer is used to make pH of less than 7.5 (preferably 3.5-6.0).

In another of the preferred alternate embodiment, the following ingredients were used:

| Terbinafine hydrochloride | 0.001 to 6% | active ingredient |
|---|---|---|
| (±) α-Tocopherol | 0.001 to 0.2% | antioxidant |
| Sodium Alginate | 0.5 to 2.0% | viscosity increasing agent |
| Carbopol 940 | 0.1 to 2.5% | viscosity increasing agent |
| Butylated Hydroxytoluene | 0.001 to 0.2% | antioxidant |
| Butylated Hydroxyanisole | 0.001 to 0.2% | antioxidant |
| Methyl 4-Hydroxybenzoate | 0.1 to 0.2% | preservative |
| Propyl 4-Hydroxybenzoate | 0.01 to 0.1% | preservative |
| 1,3-Butanediol | 2 to 20% | humectant, enhancer |
| Ethanol | 5 to 50% | solubilizer, enhancer |
| Phospholipids | 1 to 20% | solubilizer, enhancer |
| Citric Acid Monohydrate |  | buffer |
| Sodium Citrate |  | buffer |

The citrate buffer is used to make pH of less than 7.5 (preferably 3.5-6.0).

In a third preferred alternate embodiment, the following ingredients were used:

| Terbinafine hydrochloride | 0.001 to 6% | active ingredient |
|---|---|---|
| (±) α-Tocopherol | 0.001 to 0.2% | antioxidant |
| Sodium Alginate | 0.5 to 2.0% | viscosity increasing agent |
| Carbopol 940 | 0.1 to 2.5% | viscosity increasing agent |
| Butylated Hydroxytoluene | 0.001 to 0.2% | antioxidant |
| Butylated Hydroxyanisole | 0.001 to 0.2% | antioxidant |
| Methyl 4-Hydroxybenzoate | 0.1 to 0.2% | preservative |
| Propyl 4-Hydroxybenzoate | 0.01 to 0.1% | preservative |
| Propylene Glycol | 2 to 20% | humectant, enhancer |
| Cholesterol | 1 to 25% | stabilizer |
| Polysorbate 80 | 1 to 40% | solubilizer, enhancer |
| Citric Acid Monohydrate |  | buffer |
| Sodium Citrate |  | buffer |

The citrate buffer is used to make pH of less than 7.5 (preferably 3.5-6.0).

Although the embodiments are preferably made from the ingredients listed above, other alternative ingredients may also be used. These alternative ingredients include but are not limited to allylamine drugs as the active ingredient; alcohols, polyols, surfactants, complexing agents and others as the solubilizser; alcohols, fatty alcohols, fatty acids, fatty acid esters, polyols, amides, pyrrolidone derivatives, surfactants, phospholipids, terpenes and others as the enhancer; tocopherols, butylated hydroxytoluene, butylated hydroxyanisole, propyl gallate, sodium metabisulfite, sodium bisulfite and ascorbic acid and others as the antioxidant; EDTA, citric acid and others as the chelating agent; xanthan, alginate, carrageenan, cellulose derivatives, agar or other natural gums and others as the viscosity increasing agent; other types of preservatives besides methyl 4-hydroxybenzoate and propyl 4-hydroxybenzoate; 1,3-butanediol, propylene glycol, glycerin, sorbitol, polyethylene glycol and others as the humectants; and citric buffer, phosphate buffer, acetate buffer and others as the buffers.

There are other chemicals in each category of the ingredients. Some examples are:

Antioxidants: alkyl gallates such as propyl gallate, ascorbic acid, sodium sulfite, sodium bisulfite, sodium metabisulfite, alpha-tocopherols, butylated hydroxytoluene, butylated hydroxyanisole.

Chelating agent: citric acid, disodium EDTA, tetrasodium EDTA.

Humectants: glycerin, propylene glycol, 1,3-butylene glycol, sorbitol, lactic acid, methyl gluceth −10, aloe vera extract, sodium PCA, urea, polyethylene glycol 400.

Anti-freezing agents: ethanol, propylene glycol, polyethylene glycol 400, glycerin, sorbitol.

Solubilizers: surfactants such as those in the group of Tween, Span, Poloxamer, Brij, Cremophor; alcohols such as ethanol, isopropyl alcohol; polyols such as butylene glycol, propylene glycol, glycerin, sorbitol, low molecular weight polyethylene glycol; complexing agents such as cyclodextrins.

Enhancers: alcohols and alkanols such as ethanol, isopropyl alcohol, decanol; fatty alcohols such as caprylic alcohol, cetyl alcohol, stearyl alcohol; fatty acids such as oleic acid, caproic acid, capric acid, lauric acid, myristic acid, stearic acid, caprylic acid, isostearic acid, polyunsaturated linoleic acid, alpha-linolenic acid, arachidonic acid; fatty acid esters such as isopropyl myristate, isopropyl palmitate, isnonyl isononanoate, ethyl acetate; polyols such as propylene glycol, polyethylene glycol, glycerol, 1,3-butanediol, sorbitol; terpenes such as cineole, menthone, limonene, nerolidol, pinene, terpine, menthone, carvone; amides such as urea, dimethylformamide, cyclic amides such as 1-dodecylazacycloheptane-2-one (Azone) and its analogues; pyrrolidone derivatives such as 2-pyrrolidone; essential oils such as eucalyptus, chenopodium; phospholipids such as phosphatidylcholine, phosphatidylethanolamine, phosphatidylserine, phosphatidylinositol, lecithin; surfactants such as sodium lauryl sulfate, sodium palmitate, sulfosuccinates, cetrimonium bromide, alkyl betaines, fatty amine sulfates, difatty alkyl triethanolamine derivatives, sodium lauraminopropionate, acylamphoacetate, aminopropyl alkylglutamide, lanolin alcohols, polyoxyethylene alkyl phenols, polyoxyethylene fatty amine, polyoxyethylene fatty alcohol ether, polyoxyethylene fatty acid esters, sorbitan esters, glyceryl esters, polysorbates, poloxamers, polyoxythylene glycol monoethers, cetyltrimethyl ammonium bromide, benzalkonium chloride, cetylpyridinium chloride; organic acids such as salicylic acid, salicylates, citric acid.

Preservatives: methyl 4-hydroxybenzoate, propyl 4-hydroxybenzoate, benzoic acid.

Buffers: citric buffer, phosphate buffer, acetate buffer, carbonate buffer, boric buffer.

Viscosity increasing agents: natural sources such as acacia, tragacanth, agar, alginagte, sodium alginate, gellan, gelatin, carrageenan, pectin, xanthan, chitosan; cellulose derivatives such as carboxymethylcellulose sodium, ethylcellulose, hydroxyethylcellulose, methylcellulose, hydroxypropylmethylcellulose; polyethyenes; acrylic polymers such as carbomer or carbopol and its derivatives; polyvinylpyrrolidone; polyvinyl derivatives such as polyvinyl alcohol, polyvinyl acetate; block copolymers such as poloxamer; colloidally dispersed solids such as bentonite, hectorite, magnesium aluminum silicate (veegum), microcrystalline silica, colloidal silicon dioxide, montmorillonite clay; fatty alcohol such as cetyl alcohol, cetearyl alcohol, stearyl alcohol, behenyl alcohol; fatty acid such as stearic acid; waxes such as beeswax, carnauba wax, microcrystalline wax.

In the preferred embodiment of the present invention, the active ingredient is prepared in an acidic environment which alters the physicochemical properties of the active ingredient resulting in a positive charge. This positive charge and the enhancers used provide the increased effectiveness of active ingredient for topical treatment of fungal infections of the skin and skin appendages. In one preferred embodiment using terbinafine, prototype development revealed positive charge.

The positive charge can be determined by examining the pKa of the active ingredient. For example, the pKa of terbinafine is 7.10. Theoretically at a pH of 7.10, there are 50% positively charged terbinafine molecules and 50% unionized terbinafine molecules. At pH<pKa, the positively charged terbinafine is more than 50%. When pH>pKa the positively charged terbinafine is less than 50%. At pH of 5.10, there should be about 99% positively charged terbinafine and about 1% unionized terbinafine. On the other hand, at pH of 9.10, there should be about 99% unionized terbinafine and about 1% positively charged terbinafine.

Prototype measurements of zeta potential of the 0.02 g/ml terbinafine hydrochloride solution and the result is positive at pH of below 5.11. However, there are other anions in the solution, e.g., chloride ion and hydroxide ion (sodium hydroxide was used to adjust the solution pH) that make negative values of zeta potential.

| | pH | | | |
|---|---|---|---|---|
| | 3.68 | 5.11 | 7.07 | 8.73 |
| Zeta Potential (mV) | +12.1 | +31.2 | −34.0 | −58.8 |

In the preferred embodiment, the invention is applied to the skin or skin appendages including hair and nails through a dispenser and spread evenly over the treatment area. As the present invention is applied, the beads are ruptured by the orifice of the dispenser. In alternate embodiments, the orifice of the dispenser may be larger than the beads, thus the beads are ruptured by hand pressure during application. The dispenser may be a pump, tube or any commercially available container suitable for such use. No special application tool is needed.

In alternate embodiments the positively charged active ingredient plus enhancers are:
  a. dissolved directly in (or incorporated directly to) the vehicle. This includes all conventional dosage forms such as creams, gels, ointments, lotions, emulsions, solutions, suspensions and pastes.
  b. entrapped (or encapsulated) in microparticles or nanoparticles (such as microcapsules, microspheres, liposomes, microsponges) with diameter size range of 10 nanometers to 200 micrometers.
  c. entrapped in beads (0.2-10 millimeters)
  d. entrapped in microparticles or nanoparticles and then further entrapped in beads (0.2-10 millimeters)

The present invention can be applied to a corneocyte of skin, a trichocyte of hair and an onychocyte of a nail plate and corneocytes of the nail bed.

The preferred embodiments described herein are illustrative only, and although the examples given include much specificity, they are intended as illustrative of only a few possible embodiments of the invention. Other embodiments and modifications will, no doubt, occur to those skilled in the art. The examples given should be interpreted as illustrations of some of the preferred embodiments of the invention.

What is claimed is:

1. A method for topical treatment of onychomycosis in a subject in need thereof, wherein the method comprises applying to a nail of the subject a composition comprising:
  (a) about 0.001% to about 6% weight/weight positively charged terbinafine,
  (b) about 1% to about 20% weight/weight phospholipid,
  (c) at least one solubilizer selected from the group consisting of water, ethanol, polyols, glycols, surfactants, phospholipids, polysorbate 20, polysorbate 80, and complexing agents,
  (d) at least one enhancer selected from the group consisting of ethanol, alkanols, fatty alcohols, fatty acids, fatty acid esters, polyols, polysorbate 20, polysorbate 80, propylene glycol, 1,3-butanediol, terpenes, amides, cyclic amides, pyrrolidone derivatives, essential oils, phospholipids and surfactants,
  (e) at least one antioxidant,
  (f) at least one preservative,
  (g) at least one humectant selected from the group consisting of 1,3-butanediol, propylene glycol, glycerin, sorbitol, lactic acid, methyl gluceth-10, aloe vera extract, sodium PCA, and polyethylene glycol, and (h) at least one viscosity increasing agent, wherein the composition has a pH in the range of about 3.5 to about 7.0.

2. The method of claim 1, wherein the terbinafine is terbinafine HCl.

3. The method of claim 1 or 2, wherein the composition is encapsulated in microparticles or nanoparticles.

4. The method of claim 3, wherein the microparticles or nanoparticles are encapsulated in beads.

5. The method of claim 1, wherein the phospholipid is selected from the group consisting of phosphatidylcholine, phosphatidylethanolamine, phosphatidylserine, phosphatidylinositol, and lecithin.

6. The method of claim 1, wherein the composition is encapsulated in beads.

7. The method of claim 6, wherein the beads are 0.2 to 10 millimeters in diameter.

8. The method of claim 6, wherein the beads comprise microparticles or nanoparticles having a diameter of 10 nanometers to 200 micrometers.

9. The method of claim 8, wherein said microparticles or nanoparticles are selected from the group consisting of microspheres, liposomes and microsponges.

10. The method of claim 6, wherein the phospholipid is selected from the group consisting of phosphatidylcholine, phosphatidylethanolamine, phosphatidylserine, phosphatidylinositol, and lecithin.

11. The method of claim 1, wherein the antioxidant is selected from the group consisting of butylated hydroxytoluene, butylated hydroxyanisole, tocopherols, propyl gallate, alkyl gallates, sodium sulfite, sodium bisulfite, sodium metabisulfite, and ascorbic acid.

12. The method of claim 1, wherein the preservative is selected from the group consisting of methyl 4-hydroxybenzoate, propyl 4-hydroxybenzoate, and benzoic acid.

13. The method of claim 1, wherein the viscosity increasing agent is selected from the group consisting of acacia, tragacanth, agar, natural gums, alginate, sodium alginate, gellan, gelatin, carrageenan, pectin, xanthan, chitosan, cellulose derivatives, polyethylenes, carbomers, polyvinylpyrrolidone, polyvinyl acetate, polyvinyl alcohol, block copolymers, fatty alcohols, fatty acids, and waxes.

* * * * *